United States Patent [19]
Siegele et al.

[11] Patent Number: 5,948,928
[45] Date of Patent: Sep. 7, 1999

[54] MONO, DI- AND TRIFLUOROACETATE SUBSTITUTED SILANES

[75] Inventors: Frederick H. Siegele, Austin; Scott L. Battle, Marble Falls; Joel J. Kampa, Burnet, all of Tex.

[73] Assignee: Advanced Delivery & Chemical Systems, Ltd., Austin, Tex.

[21] Appl. No.: 08/757,971

[22] Filed: Dec. 5, 1996

[51] Int. Cl.[6] ........................................... C07F 7/08
[52] U.S. Cl. ............................................. 556/442
[58] Field of Search .............................. 556/442

[56] References Cited

U.S. PATENT DOCUMENTS

| | | | |
|---|---|---|---|
| 3,560,436 | 2/1971 | Szendrey | 556/442 |
| 4,892,962 | 1/1990 | Lang | 556/442 X |
| 5,194,648 | 3/1993 | Satoh et al. | 556/442 |
| 5,227,447 | 7/1993 | Sato et al. | 556/442 X |
| 5,391,796 | 2/1995 | Farnham | 556/442 |
| 5,429,995 | 7/1995 | Nishiyama et al. | |
| 5,465,766 | 11/1995 | Siegele et al. | 141/198 |
| 5,492,736 | 2/1996 | Laxman et al. | 425/579 |
| 5,562,132 | 10/1996 | Siegele et al. | 141/198 |

OTHER PUBLICATIONS

Shimogaki, Y. et al., "The Contribution of Si–O Vibration Modes to the Dielectric Constant of SiO$_2$:F Film," *1996 DUMIC Conference*, pp. 36–43.

Laxman, R.K., "Low ε Dielectrics: CVD Fluorinated Silicon Dioxides," *Semiconductor International*, 1995.

Van Schravendijk, B., et al., "Correlation Between Dielectric Reliability and Compositional Characteristics of PECVD Oxide Films," *1992 VMIC Conference*, pp. 372–378.

Carl D., et al., "Comparision of PECVD F–TEOS Films and High Density Plasma SiOF Films," *I 1995 VMIC Conference*, pp. 97–100.

Tamura, T., et al., "Preparation of Stable Fluorine–Doped Silicon Oxide Film by Biased Helicon Plasma CVD," *1996 DUMIC Conference*, pp. 231–238.

Karim, M.Z., et al., "Low Dielectric Constant Materials," *Future Fab Int'l.* 1996, pp. 213–227.

Homma, T., "Properties of Fluorinated Silicon Oxide Films Formed Using Fluorotriethoxysilane for Interlayer Dielectrics in Multilevel Interconnections," *J. Electrochem. Soc.*, 143(3):1084–1087 (1996).

Yoo, W.S., et al., "PECVD of Fluorine Doped TEOS Oxide Films Using an Alternative Dopant Source," *1996 VMIC Conference*, pp. 110–112.

M.G. Pomerantseva, et al., "Preparation of [3–(Acyloxy)propyl]–and [3–(Perfluoroacyloxy)propyl]–Alkoxysilanes," *Zhurnal Obshchei Khimii*, 42:4, pp.862–866 (Apr. 1972).

*Primary Examiner*—Paul F. Shaver
*Attorney, Agent, or Firm*—Jones, O'Keefe, Egan, Peterman

[57] ABSTRACT

Silane compounds are described having the formula:

$$Si(OR^1)_a(O_2CR^2)_bF_c$$

wherein:

R$^1$ is alkyl, alkenyl, alkynyl, aryl or benzylic and is optionally non-fluorinated, partially fluorinated or perfluorinated;

R$^2$ is —CH$_2$F, —CHF$_2$ or —CF$_3$;

a is 1, 2 or 3;

b is 1 or 2;

c is 0, 1 or 2; and wherein a+b+c equals 4. Methods of making and using these silane compounds in integrated circuit fabrication processes also are described.

27 Claims, No Drawings

MONO, DI- AND TRIFLUOROACETATE SUBSTITUTED SILANES

FIELD OF THE INVENTION

The present invention pertains to the field of mono-, di- and trifluoroacetate substituted silanes and methods of making and using mono-, di- and trifluoroacetate substituted silanes.

BACKGROUND

As the minimum feature size of the devices used in integrated circuits (ICs) continues to decrease, increased demands are placed on the materials used in the fabrication of these devices. Increased device density and number of interconnect levels in typical ICs have led to a need for materials better suited to achieve the electronic and physical properties necessary for the fabrication of these ICs. Ultra-large scale integration (ULSI) requires more efficient gap filling capabilities of sub-half micron features with high aspect ratios, i.e., the ratio of feature depth to width, which may be as high as 10:1 in some cases. In addition, decreasing the distance between metal interconnect lines requires an inter-metal dielectric (IMD) material, or insulator, with a low dielectric constant in order to minimize parasitic capacitance effects.

Desired properties for the new IMD materials are high reliability, low stress, simplicity of processing and ease of integration. Fluorine-doped silicon oxide films, which are also known as fluorinated silicate glasses (FSG), have been identified as a promising class of low dielectric constant insulators. These FSG materials exhibit enhanced gap filling capabilities over conventional boron or phosphorous doped silicate materials and due to the similarities of FSGs to conventional oxide films, these materials may be integrated into standard IC fabrication processes.

The dielectric constant of FSG materials has been shown to decrease as the fluorine content of the material increases. FSGs with dielectric contents as low as 2.3 have been reported. Shimogaki, Y. et al., "The Contribution of Si—O Vibration Modes to the Dielectric Constant of $SiO_2$:F Film," 1996 *DUMIC Conference*, pp. 36–43. Typical FSGs have dielectric constants in the range of 3.0–3.7. Laxman, R. K., "Low ε Dielectrics: CVD Fluorinated Silicon Dioxides," *Semiconductor International*, 1995.

Several methods have been described for the preparation of FSG films. One significant difference in these methods is the choice of fluorine containing precursor. For example, combinations of tetraethylorthosilicate (TEOS), an oxygen source such as $N_2O$, $O_2$ or $O_3$ and a fluorine source such as $C_2F_6$, $CF_4$, $NF_3$ and $SiF_4$ have been used in plasma-based deposition processes, such as plasma enhanced chemical vapor deposition (PECVD) processes. Van Schravendijk, B., et al., "Correlation Between Dielectric Reliability and Compositional Characteristics of PECVD Oxide Films," 1992 *VMIC Conference*, pp. 372–378; Carl, D., et al., "Comparison of PECVD F-TEOS Films and High Density Plasma SiOF Films," 1995 *VMIC Conference*, pp. 97–100; Tamura, T., et al., "Preparation of Stable Fluorine-Doped Silicon Oxide Film By Biased Helicon Plasma CVD," 1996 *DUMIC Conference*, pp. 231–238; Karim, M. Z., et al., "Low Dielectric Constant Materials," *Future Fab Int'l*, 1996, pp. 213–227. Plasma processing of $C_2F_6$ has been shown to generate $CF_3$ radicals. These $CF_3$ moieties can undergo further excitation and decomposition to yield atomic fluorine species and these species are then incorporated into the FSG film. $SiF_4$ also is believed to generate atomic fluorine species under plasma excitation and also results in fluorine species that are substituted into the silicate structure of the deposited film.

Another approach for making FSG films is to incorporate a pre-existing Si—F bond into the CVD precursor molecule. For example, a fluorotriethoxysilane ($FSi(OC_2H_5)_3$)/pure water system has been described. Homma, T., "Properties of Fluorinated Silicon Oxide Films Formed Using Fluorotriethoxysilane for Interlayer Dielectrics in Multilevel Interconnections," *J. Electrochem. Soc.*, 143(3):1084–1087 (1996). Also, systems using 1,2 bis[methyldifluorosilyl] ethane have been described. Yoo, W. S., et al., "PECVD of Fluorine Doped TEOS Oxide Films Using an Alternative Dopant Source," 1996 *VMIC Conference*, pp. 110–112; U.S. Pat. No. 5,492,736. These materials may be used in conjunction with TEOS and an oxygen source to produce the FSG films.

However, a problem believed to be common to all dual source CVD processes is that variations in the ratio of the precursors may have undesirable effects on the properties of the resulting FSG film. Also, due to the ease of fluoride elimination in perfluorinated alkyl groups directly bound to silicon, perfluoroalkylsilanes are not stable.

SUMMARY OF THE INVENTION

Mono-, di- and trifluoroacetate substituted silane compounds capable of being used as CVD precursors are described. Preferred compounds of the present invention have the following structural formula:

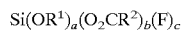

wherein:
  $R^1$ can be alkyl, alkenyl, alkynyl, aryl or benzylic groups, which $R^1$ groups can be non-fluorinated, partially fluorinated or perfluorinated;
  $R^2$ is $—CH_2F$, $—CHF_2$, or $—CF_3$;
  a is 1, 2 or 3;
  b is 1 or 2;
  c is 0, 1 or 2; and
wherein a+b+c equals 4.

Methods of preparing the invention compounds also are described. These methods preferably encompass contacting a first compound with a second compound, wherein the first compound has the formula:

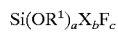

wherein:
  $R^1$ is as defined above;
  X is hydrogen or a halogen other than fluorine;
  a is 1, 2, 3 or 4;
  b is 0 or 1;
  c is 0, 1 or 2; and
wherein a+b+c equals 4 and the second compound has a formula selected from the group consisting of $[R^2C(O)]_2O$ and $R^2CO_2M$, wherein $R^2$ is $—CH_2F$, $—CHF_2$ or $—CF_3$ and M is H or a metal ion, such as alkali and alkaline earth metal ions.

These starting compounds are preferably heated and permitted to react for a sufficient time to allow conversion into the mono-, di- or trifluoroacetate substituted silane product. The reaction mixture is preferably cooled at that time and the desired products are recovered by appropriate separation techniques, such as vacuum distillation. Preferably, the invention compounds are purified to 95% or greater purity. More preferably, the invention compounds are purified to 98% or greater purity. Most preferably, the invention compounds are purified to 99.999999+% purity with respect to trace metals and have an overall purity of 99.99+%.

The preferred compounds also may be used in a process for forming fluorine-containing silicon oxide films. The preferred compounds may be used alone, or in combination with other sources of silicon, such as TEOS, and/or other sources of fluorine, such as those previously described, and in combination with an oxygen source, such as $N_2O$, $H_2O$, $O_2$ or $O_3$. Preferably, these compounds are used in a plasma enhanced chemical vapor deposition (PECVD) process. The PECVD process is preferably conducted at temperatures in the range of about 50–500° C., at pressures of about 0.2–2 Torr and with plasma power density of about 0.25 to 2 Watts/cm². The invention compounds preferably are introduced into the PECVD process, for example, by entrainment in an inert carrier gas, vaporization or direct liquid injection.

Accordingly, one object of an aspect of the present invention is to provide mono-, di- and trifluoroacetate substituted silanes and methods of preparing the same.

Another object of an aspect of the invention is to provide a single source precursor for the preparation of FSG films.

Other objects of aspects of the present invention will be apparent from the following description and the claims.

DETAILED DESCRIPTION OF THE INVENTION

A new class of mono-, di- and trifluoroacetate silane compounds is described, which compounds are suitable for use in the preparation of FSG films in microelectronic applications. These compounds contain a pendent mono-, di-, or trifluoroacetate group that is capable of undergoing plasma reactions to generate carbon dioxide and $CH_2F$, $CHF_2$ or $CF_3$ radicals. These radicals further decompose to produce fluorine species commonly found in $C_2F_6$ plasmas. Thus, the present compounds offer a single source of all essential components that are found in dual source TEOS/$C_2F_6$ PECVD systems. Therefore, the present compounds negate the need for strict gas metering that is necessary in variable composition dual source systems and can be used as replacements for TEOS/$C_2F_6$ in the preparation of FSG films. In addition, unlike compounds having perfluoroalkyl groups bound directly to silicon, the compounds of the present invention are stable under normal conditions.

Compounds of the present invention have the general formula:

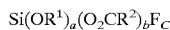

$$Si(OR^1)_a(O_2CR^2)_bF_c$$

wherein:

$R^1$ can be alkyl, alkenyl, alkynyl, aryl or benzylic groups and can be non-fluorinated, partially fluorinated or perfluorinated;

$R^2$ is —$CH_2F$, —$CHF_2$ or —$CF_3$;

a is 1, 2 or 3;

b is 1 or 2;

c is 0, 1 or 2; and wherein a+b+c equals 4.

Particular $R^1$ groups include methyl, ethyl, vinyl, propyl, butyl, pentyl, hexyl, cyclohexyl, phenyl or mixtures thereof. In addition, the $R^1$ groups may be straight chain or branched, such as in iso and tertiary structures, saturated or unsaturated and may have substituents such as alkyl, alkenyl, alkynyl, aryl or benzylic groups. Further, each $R^1$ group may be non-fluorinated, partially fluorinated or perfluorinated, i.e. fluorine saturated.

Preferably, $R^1$ is methyl, ethyl, vinyl or propyl. Most preferably, $R^1$ is ethyl.

Representative examples of compounds of the present invention include: $Si(OMe)_3(O_2CCF_3)$, $Si(OMe)_3(O_2CCHF_2)$, $Si(OMe)_3(O_2CCH_2F)$, $Si(OMe)_2(O_2CCF_3)_2$, $Si(OMe)_2(O_2CCHF_2)_2$, $Si(OMe)_2(O_2CCH_2F)_2$, $Si(OMe)(O_2CCF_3)_2F$, $Si(OMe)(O_2CCHF_2)_2F$, $Si(OMe)(O_2CCH_2F)_2F$, $Si(OMe)_2(O_2CCF_3)F$, $Si(OMe)_2(O_2CCHF_2)F$, $Si(OMe)_2(O_2CCH_2F)F$, $Si(OMe)(O_2CCF_3)F_2$, $Si(OMe)(O_2CCHF_2)F_2$, $Si(OMe)(O_2CCH_2F)F_2$, $Si(OEt)_3(O_2CCF_3)$, $Si(OEt)_3(O_2CCHF_2)$, $Si(OEt)_3(O_2CCH_2F)$, $Si(OEt)_2(O_2CCF_3)_2$, $Si(OEt)_2(O_2CCHF_2)_2$, $Si(OEt)_2(O_2CCH_2F)_2$, $Si(OEt)_2(O_2CCF_3)F$, $Si(OEt)_2(O_2CCHF_2)F$, $Si(OEt)_2(O_2CCH_2F)F$, $Si(OEt)(O_2CCF_3)_2F$, $Si(OEt)(O_2CCHF_2)_2F$, $Si(OEt)(O_2CCH_2F)_2F$, $Si(OEt)(O_2CCF_3)F_2$, $Si(OEt)(O_2CCHF_2)F_2$, $Si(OEt)(O_2CCH_2F)F_2$, $Si(OPr)_3(O_2CCF_3)$, $Si(OPr)_3(O_2CCHF_2)$, $Si(OPr)_3(O_2CCH_2F)$, $Si(OPr)_2(O_2CCF_3)_2$, $Si(OPr)_2(O_2CCHF_2)_2$, $Si(OPr)_2(O_2CCH_2F)_2$, $Si(OPr)_2(O_2CCF_3)F$, $Si(OPr)_2(O_2CCHF_2)F$, $Si(OPr)_2(O_2CCH_2F)F$, $Si(OPr)(O_2CCF_3)_2F$, $Si(OPr)(O_2CCHF_2)_2F$, $Si(OPr)(O_2CCH_2F)_2F$, $Si(OPr)(O_2CCF_3)F_2$, $Si(OPr)(O_2CCHF_2)F_2$, and $Si(OPr)(O_2CCH_2F)F_2$.

Preferably, compounds of the present invention are prepared by a transesterification reaction according to the following equation:

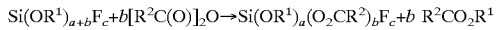

$$Si(OR^1)_{a+b}F_c + b[R^2C(O)]_2O \rightarrow Si(OR^1)_a(O_2CR^2)_bF_c + b\, R^2CO_2R^1$$

wherein a+b is 2, 3 or 4, a+b+c is 4 and the remaining variables are as defined above. The fluorinated acetate group from the acetic anhydride ($[R^2C(O)]_2O$) displaces at least one $OR^1$ group and provides the desired compounds in high yields.

A typical transesterification reaction is performed by loading the reactants into a suitable reactor under inert atmosphere. Preferably, the reactor is a dried stainless steel pressure reaction vessel. The reactor may be sealed and the contents heated to 50–200° C. for 2–48 hours. Preferably, the contents are maintained at 80–100° C. for at least about 12 hours. The reaction time should be sufficient to allow for virtually complete conversion of the reactants into the desired silane product and the ester by-product. The amount of $[R^2C(O)]_2O$ added to the reaction mixture generally determines the composition of the final silane product. For example, a 1:1 stoichiometric ratio of the starting materials generally results in a high yield of the monosubstituted mono-, di- or trifluoroacetate substituted silane, whereas a 1:2 molar ratio of the silane starting material to the mono-, di- or trifluoroacetic anhydride generally results in a high yield of the disubstituted mono-, di- or trifluoroacetate substituted silane.

The desired product may be purified by a variety of separation techniques. Preferably, the reaction mixture is transferred to a vacuum distillation apparatus and the mixture is purified to electronic grade purity by fractional distillation. Preferably, the present compounds are purified to 95+% purity. More preferably, the purity is 98+%. If the present compounds are to be used in semiconductor fabrication processes, the present compounds may be purified to 99.999999+% purity with respect to trace metals and 99.99+% overall purity.

The compounds of the present invention may be used to prepare fluorine-doped silicon oxide films. Deposition processes with the present compounds may be performed according to conventional plasma enhanced chemical vapor deposition (PECVD), low pressure chemical vapor deposition (LPCVD) and atmospheric pressure chemical vapor deposition (APCVD) processes. For example, the preferred PECVD process may be conducted at temperatures of about 50–500° C., pressures of about 200–2000 mTorr and plasma power density of about 0.25–2 watts/cm$^2$.

A variety of methods may be used to deliver the present compounds into the PECVD reactor. For example, an inert gas may act as a carrier to introduce the present compounds into the PECVD reactor. The inert gas is chosen to be a gas that does not adversely affect the formation of the FSG film. Appropriate inert gases include $N_2$, Ar and He. Alternately, a vessel containing the present compounds can be connected to the PECVD reactor and the vapor pressure of present compounds may be used to convey the present compounds into the reactor. The vessel may be heated to maintain the vapor pressure of the present compounds as the present compounds evaporate. In addition, the present compounds may be introduced into the reactor by direct liquid injection.

The present compounds may be used alone or in combination with other sources of fluorine or silicon. For example, the present compounds may be used with sources of fluorine, such as $C_2F_6$, $CF_4$ or $NF_3$, sources of silicon, such as TEOS, or combined sources of silicon and fluorine, such as $SiF_4$, $FSi(OEt)_3$ or 1,2 bis[methyldifluorosilyl]ethane. In addition, an oxygen source, such as $N_2O$, $H_2O$, $O_2$ or $O_3$, is appropriate. Thus, the present compounds may be used with a variety of other chemicals to achieve desirable FSG film properties.

The present compounds can be used to form an FSG film on a variety of substrates, including substrates composed of silicon oxides, silicon dioxide, intermetallic layers, titanium nitride and silicon nitride. Preferably, the FSG films are used as IMD layers.

A PECVD process for forming a fluorine-containing silicon oxide film on a substrate may include the following steps:

(a) establishing a plasma in a chemical-vapor deposition (CVD) reactor charged with a substrate;

(b) introducing a compound of the present invention into the CVD reactor; and (c) reacting the compound of the present invention with an oxygen source to form a fluorine-doped silicon oxide film on the substrate.

The plasma may be generated between two electrodes using either a direct current (DC-plasma) or an alternating current that is switched at a specific frequency (Rf-plasma). In DC plasma applications, a fixed voltage differential is placed between the two electrodes to generate the plasma. A DC plasma is generally used to sputter particles from the first electrode onto the second electrode. In Rf-plasma applications, the voltage on the two electrodes is generally switched at 13.56 mega-hertz (MHz). Rf-plasma is preferably used in PECVD processes.

PECVD can be used to prepare a variety of materials, such as silicon dioxide, silicon nitride, polysilicon and metal layers, and generally permits the use of lower processing temperatures by activating the reactive species. A PECVD process generally involves three basic mechanisms:

1. Electrons generated in the plasma combine with the reactants to form ions and free radicals;

2. The reactive species are absorbed on the substrate; and

3. A rearrangement of the absorbed reactive species and their reaction products occurs so as to incorporate silicon, oxygen, and fluorine into the growing FSG film.

The present compounds optionally may be used in a bulk chemical refill system for high purity chemicals. Such systems employ at least one metallic level sensor in a refillable ampule and are described in further detail in U.S. Pat. Nos. 5,465,766 and 5,562,132, which commonly assigned patents are incorporated herein by reference.

EXAMPLES

The following examples will serve as additional illustrations of methods of making and using the present compounds and should not be construed as limitations of the claimed invention. Those skilled in the art will recognize that numerous modifications can be made to the described methods without departing from the spirit of the invention.

Unless otherwise stated, the analytical data for these examples were collected using the following equipment and procedures:

$^{19}$F-NMR spectra were obtained from a General Electric-QE300 spectrometer using $CFCl_3$ as a reference (0.0 ppm).

FTIR spectra were obtained from a Nicolet Magna 560 FTIR spectrophotometer using KBr sample windows. Samples were either prepared as thin films or as a saturated vapor in nitrogen at room temperature.

Gas chromatographic (GC) data were obtained on a Hewlett Packard 5890 Series II Gas Chromatograph using HP-5, 0.32 mm×30 m capillary columns. A thermal conductivity detector was used to detect the column effluent. The temperature program was run as follows: injector and initial oven temperatures were 40° C.; initial dwell time was 5 minutes; and the temperature ramp rate was 10° C./min. with a maximum oven temperature of 300° C.

Example 1—Preparation of Triethoxysilyl Trifluoroacetate (TESTA)

Tetraethylorthosilicate (TEOS), 104 g, is loaded into a dried 1.3 L stainless steel pressure reaction vessel. A stoichiometric amount of trifluoroacetic anhydride, 105 g, is added. The reactor is sealed and the contents are heated at 80–100° C. for at least 12 hours. Preferably, the reaction is run at 80° C. for 16 hours. After sufficient time is permitted for conversion into the desired product, the reaction mixture is cooled and transferred to a vacuum distillation apparatus.

The more volatile components of the crude reaction mixture are distilled off at atmospheric pressure until the pot temperature rises above 60° C. The reaction mixture is then allowed to cool to room temperature and the pressure is reduced to 11 Torr. A 7 foot fractionating column is used to provide sufficient purity by vacuum distillation. TESTA distills at 59° C./11 Torr.

Analytical data for TESTA:

$^{19}$F-NMR: $\delta_{CF3}$=−76.7 ppm (singlet).

FTIR: A comparison of the FTIR spectrum for TESTA prepared according to this method with a published TEOS spectrum shows two primary differences between the spectra. Additional absorbances are found in the TESTA spectrum due to both the fluorocarbon ($CF_3$) and the carbonyl (C=O) groups that are associated with the trifluoroacetate group, namely $v_{CF3}$ at 1226 cm$^{-1}$ and $v_{C=O}$ at 1786 cm$^{-1}$.

GC Retention Time: TESTA elutes at 8.0 minutes.

Example 2—Preparation of Triethoxysilyl Difluoroacetate

Triethoxysilyl difluoroacetate may be prepared according to the teachings of Example 1 by replacing 87 g of difluoroacetic anhydride for the trifluoroacetic anhydride.

Example 3—Preparation of Diethoxyfluorosilyl Trifluoroacetate (DEFSTA)

DEFSTA may be prepared and purified according to the teachings of Example 1 by replacing TEOS with 90 g of triethoxyfluorosilane. The same procedure may be used to vacuum distill DEFSTA as described in Example 1, but the temperature and pressures are modified. In this case, DEFSTA distills at 37° C. and 20 Torr.

Analytical data:

$^{19}$F-NMR: $\delta_{CF_3}$=−76.6 ppm (singlet);

$\delta_{SiF}$=+47.1 ppm (singlet).

FTIR: The FTIR spectrum of DEFSTA prepared according to this method contains all of the absorbances associated with the ethoxy groups in TEOS and TESTA and the trifluoroacetate group in TESTA. The primary difference of the FTIR spectrum of DEFSTA is an additional absorbance due to a fluorine-silicon bond, namely $\nu_{SiF}$ at 917 cm$^{-1}$. The absorbances due to the CF$_3$ and C=O groups also have shifted from the TESTA spectrum, namely $\nu_{CF_3}$ is now at 1238 cm$^{-1}$ and $\nu_{C=O}$ is now at 1796 cm$^{-1}$.

GC Retention Time: DEFSTA elutes at 2.8 minutes.

Example 4—Preparation of Diethoxyfluorosilyl Difluoroacetate

Diethoxyfluorosilyl difluoroacetate may be prepared and purified according to the teachings of Example 1 by replacing TEOS with 90 g of triethoxyfluorosilane and replacing trifluoroacetic anhydride with 75 g of difluoroacetic anhydride.

Example 5—Alternate Preparation of Mono-, Di- and Trifluoroacetate Substituted Silanes The invention compounds also may be prepared by the displacement of an alkoxy group using a fluorinated acid to form a free alcohol and an acetate adduct of the silane according to the following equation:

Si(OR$^1$)$_{a+b}$F$_c$+bR$^2$C(O)OH→Si(OR$^1$)$_a$(O$_2$CR$^2$)$_b$F$_c$+bR$^1$OH wherein the variables are the same as those described above. For example, TESTA may be prepared and purified according to the teachings of Example 1 by replacing 57 g of the trifluoroacetic acid for the trifluoroacetic anhydride.

Example 6—Second Alternate Preparation of Mono-, Di- and Trifluoroacetate Substituted Silanes As a second alternate route for preparation of the invention compounds, the acetate adduct of the silane may be formed by a salt elimination reaction between a metal salt of the acetate and a halo-silane according to the following equation:

Si(OR$^1$)$_a$X$_b$F$_c$+bR$^2$(O)O$^-$M$^+$→Si(OR$^1$)$_a$(O$_2$CR$^2$)$_b$F$_c$+bMX wherein X is hydrogen or a halogen other than fluorine, M is a metal ion such as an alkali or alkaline earth metal ion, including but not limited to Na$^+$ and K$^+$ and the remaining variables are as described above.

For example, TESTA may be prepared according to this method as follows: In a round bottom flask chilled to −20° C., 70 g of the sodium salt of trifluoroacetic acid is slurried in 500 ml of diethyl ether. Triethoxysilyl chloride, 100 g, is dissolved in 200 ml diethyl ether and placed in a pressure equalizing addition funnel attached to the reaction flask. With vigorous stirring the silane solution is slowly dripped into the reaction flask over a 2 hour period. Stirring is continued as the reactor is allowed to warm to room temperature. The crude reaction mixture is filtered and then vacuum distilled according to the teachings of Example 1.

Example 7—FSG Films Produced with TESTA and DEFSTA

FTIR studies of TESTA and DEFSTA produced ceramic thin films on KBr window material were performed by exposing TESTA and DEFSTA samples to moist air. The resulting films provided FTIR spectra indicative of FSG films. Prominent absorbances were observed for both the Si—O and Si—F bonds present in the film, namely $\nu_{Si-O}$ at 1093 cm$^{-1}$ and 795 cm$^{-1}$ and $\nu_{SiF}$ at 933 cm$^{-1}$.

Example 8—Preparation of FSG Films Using TESTA

TESTA is diluted 10:1 in helium prior to introduction into the deposition chamber. Oxygen is introduced at about 60 cc/min. During the deposition process, a total mass flow rate of about 80 cm$^3$/min is maintained through the chamber. The pressure is maintained at about 2 Torr. The Rf electrodes are arranged in a parallel plate geometry with a spacing of 10 cm. Plasma power is maintained at about 50 W at a frequency of 13.56 MHz.

Those skilled in the art will recognize that various modifications of the described methods can be made to prepare additional compounds encompassed by the present invention. In addition, the compounds and methods described herein may be used separately or in combinations thereof to realize the present invention in diverse forms.

We claim:

1. A compound having the formula:

Si(OR$^1$)$_a$(O$_2$CR$^2$)$_b$F$_c$ wherein:

R$^1$ is alkyl, alkenyl, alkynyl, aryl or benzylic and is optionally non-fluorinated, partially fluorinated or perfluorinated;

R$^2$ is —CH$_2$F, —CHF$_2$ or —CF$_3$;

a is 1,2 or 3;

b is 1 or 2;

c is 0, 1 or 2; and wherein a+b+c equals 4 with the proviso that when a is 3 at least one R$^1$ is other than ethyl.

2. A compound of claim 1 wherein R$^1$ is methyl, ethyl, vinyl, propyl, butyl, pentyl, hexyl, cyclohexyl or phenyl.

3. A compound of claim 1 wherein R$^1$ is methyl, ethyl, vinyl or propyl.

4. A compound of claim 1 wherein R$^1$ is ethyl.

5. A compound having the formula:

Si(OR$^1$)$_2$(O$_2$CR$^2$)$_b$F$_c$ wherein:

R$^1$ is alkyl, alkenyl, alkynyl, aryl or benzylic and is optionally non-fluorinated, partially fluorinated or perfluorinated;

R$^2$ is —CH$_2$F, —CHF$_2$ or —CF$_3$;

a is 2;

b is 1; and c is 1.

6. A compound of claim 5 wherein R$^1$ is methyl, ethyl, vinyl or propyl.

7. A compound of claim 1 wherein $R^1$ is ethyl.

8. A compound selected from the group consisting of $Si(OMe)_3(O_2CCF_3)$, $Si(OMe)_3(O_2CCHF_2)$, $Si(OMe)_3(O_2CCH_2F)$, $Si(OMe)_2(O_2CCF_3)_2$, $Si(OMe)_2(O_2CCHF_2)_2$, $Si(OMe)_2(O_2CCH_2F)_2$, $Si(OMe)(O_2CCF_3)_2F$, $Si(OMe)(O_2CCHF_2)_2F$, $Si(OMe)(O_2CCH_2F)_2F$, $Si(OMe)_2(O_2CCF_3)F$, $Si(OMe)_2(O_2CCHF_2)F$, $Si(OMe)_2(O_2CCH_2F)F$, $Si(OMe)(O_2CCF_3)F_2$, $Si(OMe)(O_2CCHF_2)F_2$, $Si(OMe)(O_2CCH_2F)F_2$, $Si(OEt)_3(O_2CCHF_2)$, $Si(OEt)_3(O_2CCH_2F)$, $Si(OEt)_2(O_2CCF_3)_2$, $Si(OEt)_2(O_2CCHF_2)_2$, $Si(OEt)_2(O_2CCH_2F)_2$, $Si(OEt)_2(O_2CCF_3)F$, $Si(OEt)_2(O_2CCHF_2)F$, $Si(OEt)_2(O_2CCH_2F)F$, $Si(OEt)(O_2CCF_3)_2F$, $Si(OEt)(O_2CCHF_2)_2F$, $Si(OEt)(O_2CCH_2F)_2F$, $Si(OEt)(O_2CCF_3)F_2$, $Si(OEt)(O_2CCHF_2)F_2$, $Si(OEt)(O_2CCH_2F)F_2$, $Si(OPr)_3(O_2CCF_3)$, $Si(OPr)_3(O_2CCHF_2)$, $Si(OPr)_3(O_2CCH_2F)$, $Si(OPr)_2(O_2CCF_3)_2$, $Si(OPr)_2(O_2CCHF_2)_2$, $Si(OPr)_2(O_2CCH_2F)_2$, $Si(OPr)_2(O_2CCF_3)F$, $Si(OPr)_2(O_2CCHF_2)F$, $Si(OPr)_2(O_2CCH_2F)F$, $Si(OPr)(O_2CCF_3)_2F$, $Si(OPr)(O_2CCHF_2)_2F$, $Si(OPr)(O_2CCH_2F)_2F$, $Si(OPr)(O_2CCF_3)F_2$, $Si(OPr)(O_2CCHF_2)F_2$, and $Si(OPr)(O_2CCH_2F)F_2$.

9. A compound selected from the group consisting of, $Si(OEt)_2(O_2CCF_3)_2$, $Si(OEt)_3(O_2CCH_2F)$, $Si(OEt)_3(O_2CCHF_2)$, $Si(OEt)_2(O_2CCHF)_2$, $Si(OEt)_2(O_2CCF_3)F$, $Si(OEt)_2(O_2CCH_2F)F$ and $Si(OEt)_2(O_2CCHF_2)F$.

10. A compound of claim 1 wherein $R^1$ is ethyl and $R_2$ is —$CF_3$.

11. A compound of claim 10 wherein a is 2 and b is 1.

12. A compound of claim 10 wherein a is 1 and b is 2.

13. A method of synthesizing a mono-, di- or trifluoroacetate substituted silane, comprising the step of:

contacting a first compound with a second compound, wherein the first compound has a formula:

$$Si(OR^1)_aX_bF_c$$

wherein:

$R^1$ is alkyl, alkenyl, alkynyl, aryl or benzylic and is optionally non-fluorinated, partially fluorinated or perfluorinated;

X is hydrogen or a halogen other than fluorine;

a is 1, 2, 3 or 4;

b is 0 or 1;

c is 0, 1 or 2; and wherein a+b+c equals 4; and the second compound has a formula selected from the group consisting of:

$$[R^2C(O)]_2O \text{ and } R^2C(O)OM$$

wherein:

$R^2$ is —$CH_2F$, —$CHF_2$ or —$CF_3$; and

M is H or a metal ion selected from the group consisting of alkali and alkaline earth metals.

14. A method of claim 13 wherein $R^1$ is methyl, ethyl, vinyl, propyl, butyl, pentyl, hexyl, cyclohexyl or phenyl.

15. A method of claim 13 wherein $R^1$ is methyl, ethyl, vinyl or propyl.

16. A method of claim 13 wherein $R^1$ is ethyl.

17. A method of claim 16 wherein $R^2$ is —$CF_3$.

18. A method of claim 16 wherein c is 0.

19. A method of claim 13 wherein the second compound is trifluoroacetic anhydride.

20. A method of claim 19 wherein the first compound is triethoxyfluorosilane.

21. A method of claim 19 wherein the first compound is tetraethylorthosilicate.

22. A compound having the formula:

$$Si(OR^1)_a(O_2CR^2)_bF_c$$

wherein:

$R^1$ is alkyl, alkenyl, alkynyl, aryl or benzylic and is optionally non-fluorinated, partially fluorinated or perfluorinated;

$R^2$ is —$CH_2F$, —$CHF_2$ or —$CF_3$;

a is 1, 2 or 3;

b is 1 or 2;

c is 1 or 2; and where a+b+c equals 4.

23. A compound having the formula:

$$Si(OR^1)_a(O_2CR^2)_bF_c$$

wherein:

$R^1$ is alkyl, alkenyl, alkynl, aryl or benzylic and is optionally non-fluorinated, partially fluorinated or perfluorinated;

$R^2$ is —$CH_2F$, —$CHF_2$, or —$CF_3$, a is 1, 2 or 3;

b is 2;

c is 0, 1 or 2; and wherein a+b+c equals 4.

24. A compound having the formula:

$$Si(OR^1)_a(O_2CR^2)_bF_C$$

wherein:

$R^1$ is alkyl, alkenyl, alkynyl, aryl or benzylic and is optionally non-fluorinated, partially fluorinated or perfluorinated;

$R^2$ is —$CH_2F$, —$CHF_2$ or —$CF_3$;

a is 1, 2 or 3;

b is 1 or 2;

c is 0, 1 or 2; and wherein a+b+c equals 4 with the proviso that when b=2, $R^2$ is other than —$CF_3$.

25. A compound having the formula:

$$Si(OR^1)_a(O_2CR^2)_bF_c$$

wherein:

$R^1$ is alkyl, alkenyl, alkynyl, aryl or benzylic and is optionally non-fluorinated, partially fluorinated or perfluorinated;

$R^2$ is —$CH_2F$, —$CHF_2$ or —$CF_3$;

a is 2;

b is 1;

c is 0, 1 or 2; and wherein a+b+c equals 4.

26. A compound having the formula:

$$Si(OR^1)_a(O_2CR^2)_bF_c;$$

wherein:

$R^1$ is alkyl, alkenyl, alkynyl, aryl or benzylic and is optionally non-fluorinated, partially fluorinated or perfluorinated.

$R^2$ is —$CH_2F$, —$CHF_2$ or —$CF_3$ a is 1;

b is 2;

c is 0, 1 or 2; and wherein a+b+c equals 4.

27. A compound having the formula:

$$Si(OR^1)_a(O_2CR^2)_bF_c$$

wherein:

$R^1$ is alkyl, alkenyl, alkynyl, aryl or benzylic and is optionally non-fluorinated, partially fluorinated or perfluorinated;

$R^2$ is —$CH_2F$, —$CHF_2$ or —$CF_3$ a is 1 or 2;

b is 1 or 2;

c is 0, 1 or 2; and wherein a+b+c equals 4.

* * * * *